United States Patent
Ye

(10) Patent No.: US 12,247,696 B2
(45) Date of Patent: Mar. 11, 2025

(54) AUTOMATIC COUPLING AGENT FEEDER

(71) Applicant: Foshan Pingchuang Medical Technology Co., Ltd., Foshan (CN)

(72) Inventor: Jiansheng Ye, Shenzhen (CN)

(73) Assignee: Poshan Pingchuang Medical Technology Co., Ltd., Foshan (CN)

( * ) Notice: Subject to any disclaimer, the term of this patent is extended or adjusted under 35 U.S.C. 154(b) by 0 days.

(21) Appl. No.: 18/587,791

(22) Filed: Feb. 26, 2024

(65) Prior Publication Data

US 2024/0191837 A1   Jun. 13, 2024

(51) Int. Cl.
*F16N 1/00* (2006.01)
*A61B 90/00* (2016.01)
*A61M 35/00* (2006.01)

(52) U.S. Cl.
CPC ............ *F16N 1/00* (2013.01); *A61B 90/08* (2016.02); *A61M 35/00* (2013.01)

(58) Field of Classification Search
CPC .......... F16N 1/00; A61B 90/08; A61M 35/00
See application file for complete search history.

(56) References Cited

U.S. PATENT DOCUMENTS

| | | | | |
|---|---|---|---|---|
| 1,929,231 A | * | 10/1933 | Yirava | F16N 13/10 222/14 |
| 6,311,868 B1 | * | 11/2001 | Krietemeier | G01F 11/28 222/642 |
| 8,061,918 B2 | * | 11/2011 | Skalitzky | A47K 5/12 222/372 |
| 2012/0248150 A1 | * | 10/2012 | Yang | A47K 5/1217 222/571 |
| 2014/0197197 A1 | * | 7/2014 | Kamen | C02F 1/325 222/52 |
| 2015/0273513 A1 | * | 10/2015 | Buckalter | B05B 12/122 222/146.2 |
| 2019/0008331 A1 | * | 1/2019 | Yan | A47K 5/12 |

* cited by examiner

*Primary Examiner* — Vishal Pancholi

(57) ABSTRACT

Embodiments provide an automatic coupling agent feeder, including a housing, a coupling agent storage container, a feed pump, a heating insulation mechanism, a control device, and a discharge mechanism. The discharge mechanism is provided with a discharge port located outside the housing. The control device is electrically connected to the feed pump and the heating insulation mechanism; the feed pump is connected to the coupling agent storage container and the discharge mechanism, respectively, through a convey pipeline, and the heating insulation mechanism is provided outside the convey pipeline between the feed pump and the discharge mechanism. Adoption of the above technical solutions does not need to manually squeeze the coupling agent container, improve the efficiency of the operator, and the comfort of the coupling agent and human contact, in addition, installation of the parts inside the automatic coupling agent feeder internal parts is more compact.

9 Claims, 7 Drawing Sheets

AUTOMATIC COUPLING AGENT FEEDER

TECHNICAL FIELD

The present disclosure relates to the technical field of coupling agent feeding, and specifically relates to an automatic coupling agent feeder.

BACKGROUND

The coupling agent is used for ultrasound diagnostic equipment and Doppler blood flow meters, suitable for obstetrics and gynecology, digestive system, urinary system, nervous system, neonatal, thyroid, and breast examinations. It facilitates the coupling of the ultrasound probe and enhances image clarity.

Currently, the coupling agent is generally packaged inside coupling agent storage containers. When medical personnel use ultrasound diagnostic equipment to examine patients, they typically hold the ultrasound probe with one hand and squeeze the coupling agent from the packaging onto the skin surface of the area to be examined with the other hand. Then, they use the ultrasound probe to conduct the examination on the area where the coupling agent has been applied. As the remaining amount of the coupling agent in the storage container decreases, it becomes more difficult for the user to squeeze out the coupling agent, which is time-consuming and labor-intensive. Additionally, there may be residual amounts of the coupling agent in the storage container that cannot be manually squeezed out, leading to waste and increased usage costs. At the same time, the temperature of the coupling agent differs significantly from that of the human body, and its cool temperature when in contact with the body can easily cause discomfort for the patient. The current method of heating the coupling agent involves individually placing each coupling agent storage container into a heater, which is inconvenient and adds extra workload for the physician.

SUMMARY

The present disclosure, in order to overcome at least one of the defects described in the above mentioned prior art, provides an automatic coupling agent feeder, which does not need to manually squeeze the coupling agent container, improves the efficiency of the operator, and improves the comfort of the coupling agent when it is in contact with the human body, in addition to more compact installation of the parts inside the automatic coupling agent feeder, and at the same time reduces the bacteria in the coupling agent, and reduces the risk of infection.

In order to realize the above objects, the present disclosure adopts the following technical solution: an automatic coupling agent feeder comprises: a housing, a coupling agent storage container, a feed pump, a heating insulation mechanism, a control device, and a discharge mechanism; the coupling agent storage container and the feed pump are provided in the housing, the discharge mechanism is provided with a discharge port located outside the housing; the control device is provided on the housing and is electrically connected to the feed pump and the heating insulation mechanism; the feed pump is connected to the coupling agent storage container and the discharge mechanism, respectively, by means of a convey pipeline, and the heating insulation mechanism is provided outside the convey pipeline between the feed pump and the discharge mechanism.

Optionally, the automatic coupling agent feeder further comprises an ultraviolet sterilizer provided on the convey pipeline between the coupling agent storage container and the feed pump.

Optionally, the discharge mechanism comprises a liquid solenoid valve connected to an outlet end of the convey pipeline, and electrically connected to the control device.

Optionally, the control device comprises a control circuit board, a discharge switch, an operate panel, a ballast and a power supply assembly; the control circuit board, the ballast and the power supply assembly are provided in the housing, the operate panel is provided on the housing and is electrically connected to the control circuit board; the power supply assembly is electrically connected to the control circuit board; the ultraviolet sterilizer is electrically connected to the control circuit board by the ballast.

Optionally, the power supply assembly comprises a charge socket embedded in the housing and electrically connected to the control circuit board.

Optionally, the power supply assembly further comprises a power board provided in the housing, and the charge socket is electrically connected to the control circuit board via the power board.

Optionally, the power supply assembly further comprises a power switch provided on the housing, and is electrically connected to the power board.

Optionally, the housing is provided with a spacer for separating an inner cavity of the housing into a tank cavity and an electrical cavity, the coupling agent storage container is detachably mounted in the tank cavity; the tank cavity is provided with a support plate perpendicular to the spacer, the support plate is provided with a tank interface adapted with an opening of the coupling agent storage container; the charge socket and the power switch are both provided on a side of the housing adjacent to the tank cavity, the ultraviolet sterilizer, the heating insulation mechanism, the feed pump, the power board, the control circuit board and the ballast are all fixed in the electrical cavity, and the operate panel is provided on a side of the housing adjacent to the electrical cavity.

Optionally, the tank interface is provided with a puncture portion with a conical shape, and the puncture portion is provided with a number of through holes spaced apart in communication with the tank interface.

Optionally, the housing has an opening located at a top of the tank cavity, and the housing is hingedly connected to a top cover for opening or closing the opening of the tank cavity.

Optionally, a receiving tray is provided on the housing and located right below the discharge port.

Optionally, the discharge mechanism comprises a first grip and an ultrasonic wave probe; the first grip is provided outside the housing, and the discharge port is provided on the first grip; the discharge port is connected to the feed pump through the convey pipeline; and the first grip is provided with a connecting portion for adapting to the ultrasonic wave probe.

Optionally, an automatic coupling agent feeder comprises: a housing, a coupling agent storage container, a feed pump, a heating insulation mechanism, a control device and a discharge mechanism; the coupling agent storage container, the feed pump and the discharge mechanism are all provided in the housing; the feed pump is connected to the coupling agent storage container and the discharge mechanism through a convey pipeline respectively; the discharge mechanism comprises a second grip provided outside the housing and provided with a discharge port; the discharge port is connected to an outlet end of the feed pump through the convey pipeline; the heating insulation mechanism is provided on the convey pipeline and is located inside the second grip; the control device is electrically connected to the feed pump and the heating insulation mechanism, respectively.

The beneficial effects of the present disclosure after adopting the above technical solutions are:

1. By using the heating insulation device to heat and insulate the coupling agent, the temperature of the coupling agent can be brought closer to body temperature when it is dispensed from the outlet, thus enhancing comfort upon contact with the human body. Additionally, by utilizing a sterilizer to disinfect the coupling agent, it is possible to reduce the presence of bacteria in the coupling agent, thereby lowering the risk of infection.
2. The heating insulation mechanism is mounted outside the convey pipeline between the feed pump and the discharge mechanism, in this manner, making the structure of the automatic coupling agent feeder more compact.
3. Users are able to unscrew the bottle cap of the coupling agent storage container without needing to tear off the thin film on the opening thereof. This allows for stable installation of the coupling agent storage container in the tank cavity by rotating it onto the tank interface, effectively preventing the accidental detachment of the storage container from the tank interface due to collision. Once the coupling agent storage container is mounted on the tank interface, the puncture portion can open the film for use, avoiding contamination of the tank cavity due to spilling during the mounting process after tearing the film of the coupling agent storage container.
4. The ultraviolet sterilizer is connected to the convey pipeline. The ultraviolet sterilizer is electrically connected to the control device via wires. The ultraviolet sterilizer and the feed pump are sequentially provided along the path of the convey pipeline.

BRIEF DESCRIPTION OF DRAWINGS

In order to more clearly illustrate the technical solutions in the embodiments according to the present disclosure or prior art, the figures to be used in the description of the embodiments or prior art will be briefly introduced below. It will be obvious that the figures in the following description are only some of the embodiments of the present disclosure, and that for a person of ordinary skill in the field, other figures can be obtained based on the figures without inventive efforts.

Figure 1:
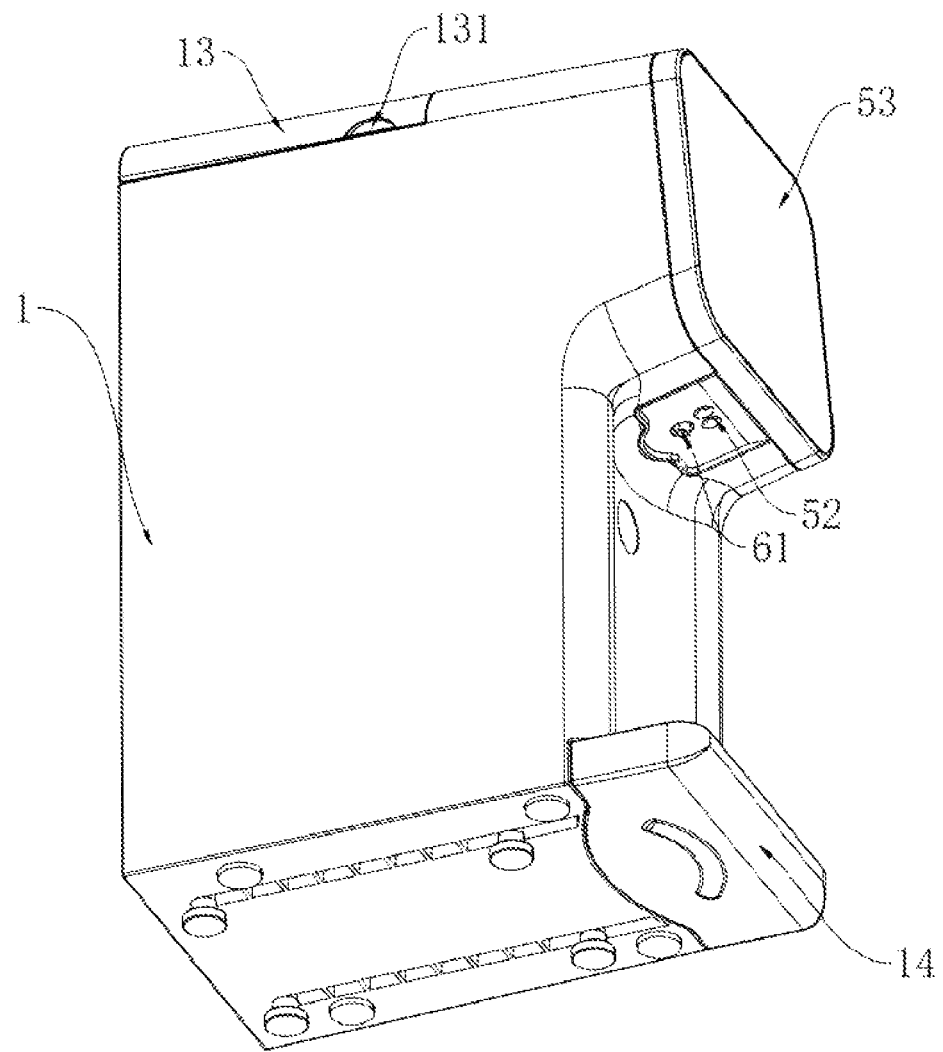
FIG. 1 is a schematic diagram of the structure of Embodiment 1.

NOTE OF REFERENCE SIGNS 1, housing; 2, coupling agent storage container; 3, feed pump; 4, heating insulation mechanism; 5, control device; 6, liquid solenoid valve; 61, discharge port; 7, convey pipeline; 8, ultraviolet sterilizer; 51, control circuit board; 52, discharge switch; 53, operate panel; 54, ballast; 55, charge socket; 56, power switch; 11, spacer; 12, support plate; 121, tank interface; 122, puncture portion; 123, through hole; 13, top cover; 14, receiving tray; 101, tank cavity; 102, electrical cavity; 111, insertion groove; 124, insertion block; 31, fix ring; 81, clamping member; 131, groove; 15, first grip; 16, ultrasonic probe; 17, connecting portion; 18, second grip ; 181, heating switch.

DESCRIPTION OF EMBODIMENTS

The present disclosure is described in further detail below in conjunction with the figures.

This specific embodiment is only an explanation of the present disclosure, which is not a limitation of the present disclosure, and the person skilled in the art may make modifications to this embodiment without inventive contribution as needed after reading this specification, but as long as it is within the scope of the claims of the present disclosure it is protected by the patent law.

It should be noted that when an element is referred to as "fixed to" or "provided on" another element, it may be directly on the other element or indirectly on the other element. When an element is referred to as "connected to" another element, it may be connected directly to the other element or indirectly to the other element.

It should be understood that the terms "length", "width", "upper", "lower", "front", "rear", "left", "right", "vertical", "horizontal", "top", "bottom", "inside", "outside" and the like indicate orientations or positional relationships based on those shown in the figures, and are intended only to facilitate the description of the present disclosure and to simplify the description, and are not intended to indicate or imply that the device or element referred to must have a particular orientation, be constructed and operated in a particular orientation, and therefore are not to be construed as a limitation of the present disclosure.

Furthermore, the terms "first" and "second" are used for descriptive purposes only and are not to be understood as indicating or implying relative importance or implicitly specifying the number of technical features indicated. Thus, a feature defined with the terms "first", "second" may expressly or impliedly include one or more such features. In some descriptions of the present disclosure, "more than one" means two or more, unless otherwise expressly and specifically limited.

Embodiment 1

The embodiment relates to an automatic coupling agent feeder, as shown in FIGS. 1-5, a housing 1, a coupling agent storage container 2, a feed pump 3, a heating insulation mechanism 4, a control device 5 and a discharge mechanism.

Figure 4:
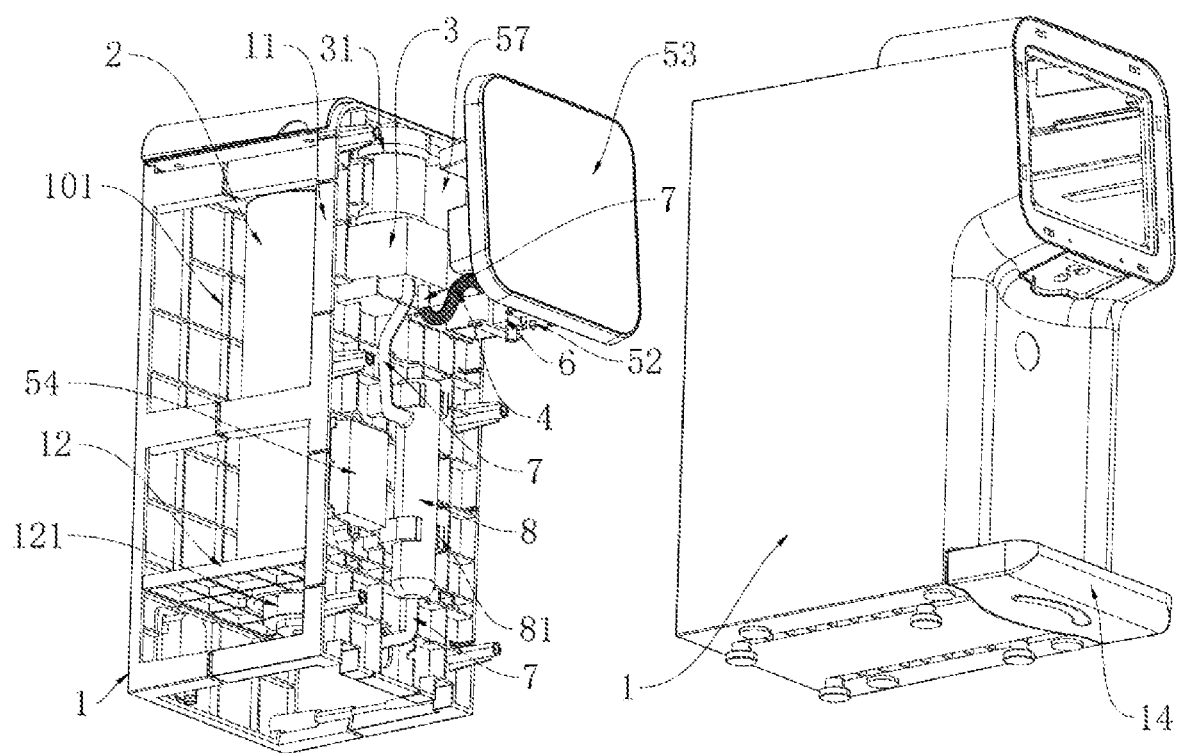
FIG. 4 shows an exploded schematic diagram of Embodiment 1.

The coupling agent storage container 2 and the feed pump 3 are provided in the housing 1, and the discharge mechanism is provided with a discharge port 61 located outside the housing 1. A control device 5 is provided on the housing 1, and is electrically connected to the feed pump 3 and the heating insulation mechanism 4. The feed pump 3 is connected to the coupling agent storage container 2 and the discharge mechanism through the convey pipeline 7, the heating insulation mechanism 4 is provided outside the convey pipeline 7 between the feed pump 3 and the discharge mechanism, and the convey pipeline 7 can be a silicone pipeline. As shown in FIG. 4, the heating insulation mechanism 4 is provided on the convey pipeline 7, such that the structure of the automatic coupling agent feeder can be more compact. The automatic coupling agent feeder adopts an external power supply. The heating insulation mechanism 4 is composed of a flexible heating sleeve.

In one embodiment, the control device 5 controls the feed pump 3, the heating insulation mechanism 4 to work to realize that the feed pump 3 delivers the coupling agent from the coupling agent storage container 2 through the convey pipeline 7 inside the heating insulation mechanism 4, heating the coupling agent to a temperature suitable for patient skin contact, and delivering it to the ultrasound probe beneath the discharge port 61.

Optionally, in some embodiments, a temperature sensor is provided between the convey pipeline and the heating insulation mechanism 4, or is provided between inside the convey pipeline between the feed pump 3 and the discharge mechanism. The temperature sensor is electrically connected to the controller, and the control circuit board detects the temperature of the coupling agent and insulates the coupling agent through the temperature sensor.

Figure 3:
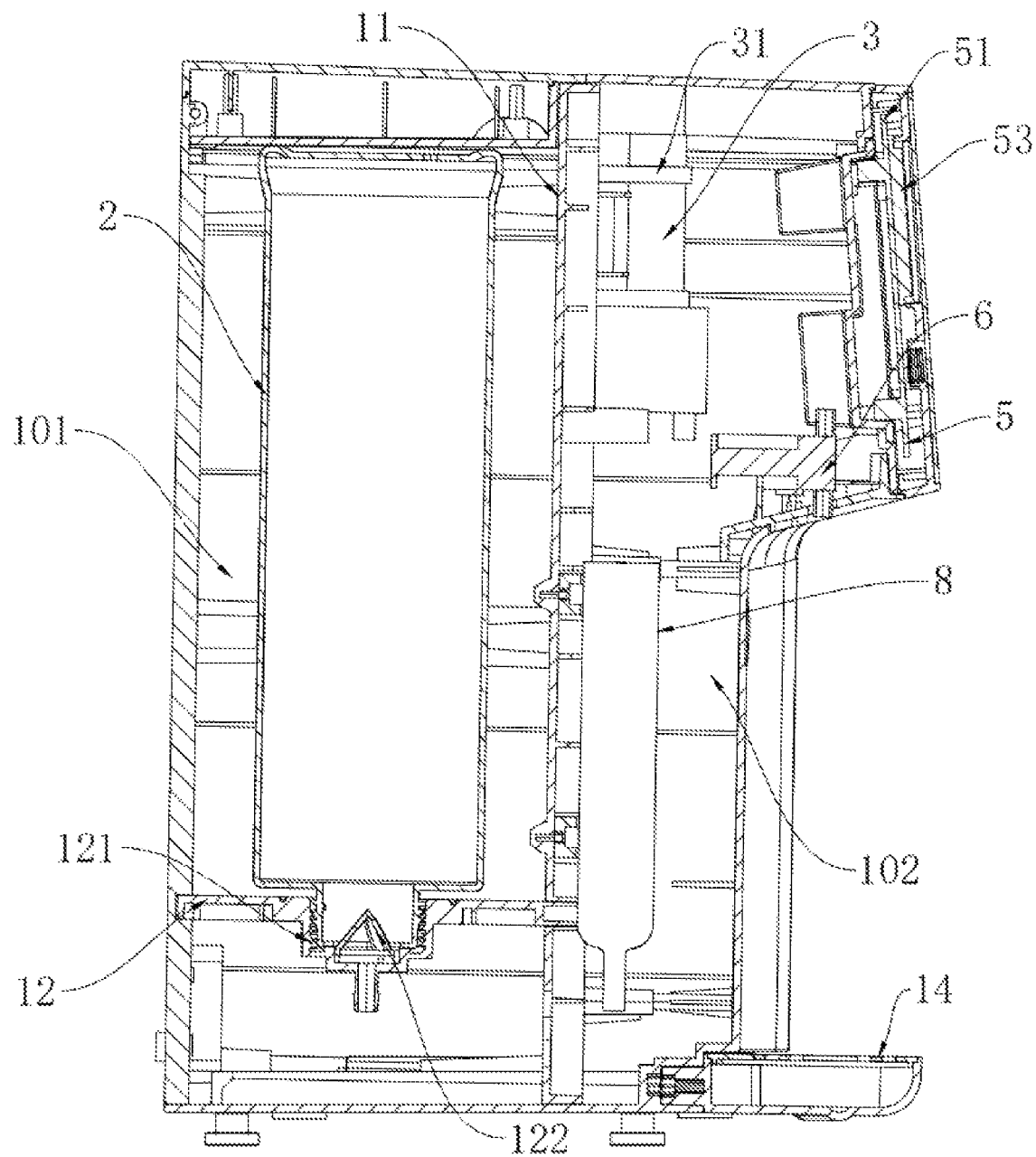
FIG. 3 is a cross-sectional view of the removal of the convey pipeline and the heating insulation mechanism in Embodiment 1.
Figure 5:
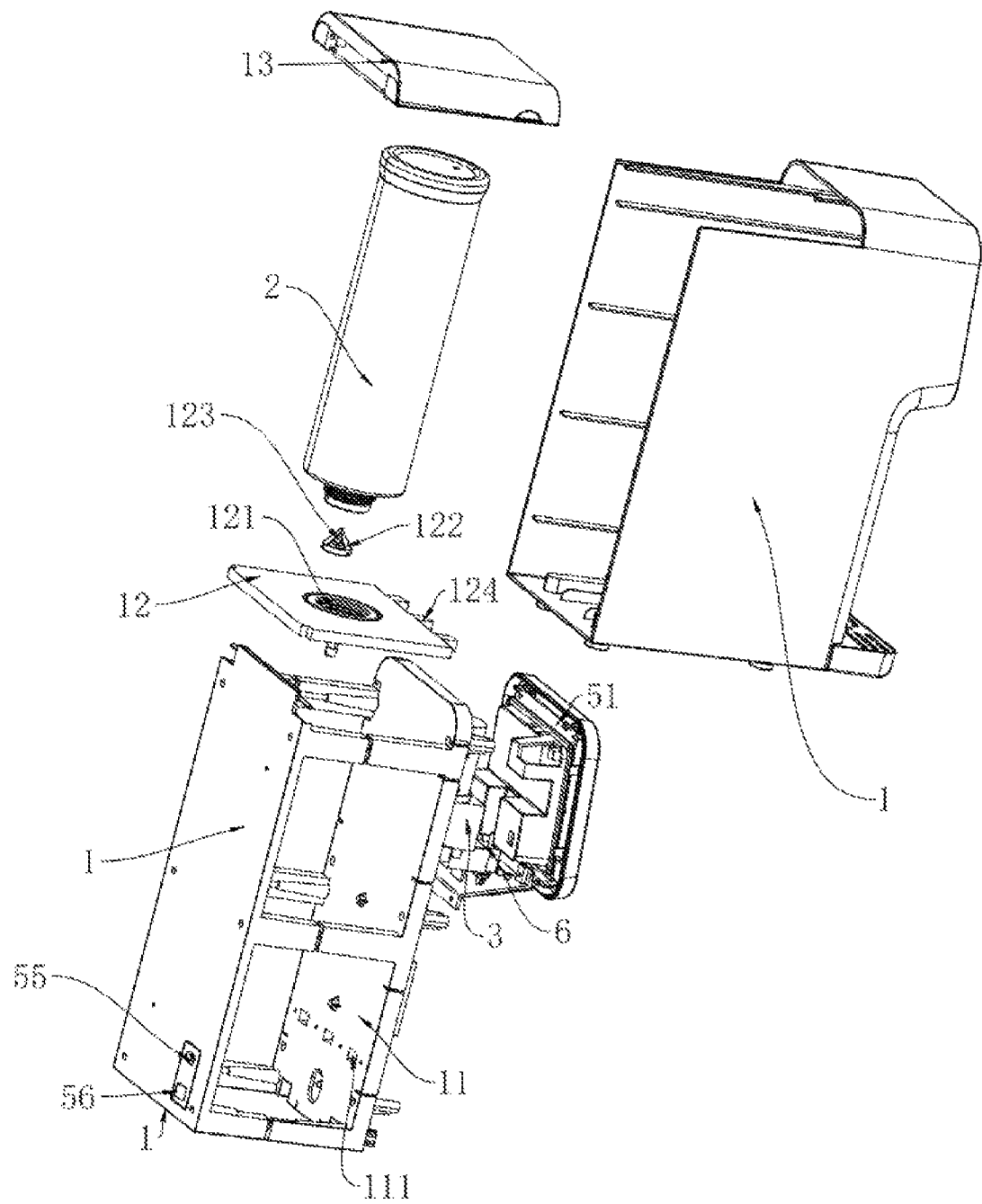
FIG. 5 is an exploded schematic diagram of the removal of the convey pipeline and the heating insulation mechanism in Embodiment 1.

Optionally, as shown in FIGS. 3-5, the automatic coupling agent feeder further comprises an ultraviolet sterilizer 8, the ultraviolet sterilizer 8 is provided on the convey pipeline 7 between the coupling agent storage container 2 and the feed pump 3. The ultraviolet sterilizer 8 is in communication with the convey pipeline 7. The ultraviolet sterilizer 8 is electrically connected to the control device 5 via a wire. In the present embodiment, the ultraviolet sterilizer 8 and the feed pump 3 are provided sequentially along the path of the convey pipeline 7.

Optionally, as shown in FIGS. 3-5, in order to make the discharging of the coupling agent more accurate and reduce the waste when the coupling agent is discharged, the discharge mechanism includes a liquid solenoid valve 6, the liquid solenoid valve 6 is connected to the outlet end of the convey pipeline 7, and the liquid solenoid valve 6 is electrically connected to the control device 5. Preferably, the liquid solenoid valve 6 is provided in the housing 1, and the discharge port 61 is located on the liquid solenoid valve 6.

It should be noted that, as shown in FIGS. 3-5, the control device 5 includes a control circuit board 51, a discharge switch 52, an operate panel 53, a ballast 54 and a power supply assembly. The control circuit board 51, the ballast 54 and the power supply assembly are provided in the housing 1, and the operate panel 53 is provided on the housing 1 and is electrically connected to the control circuit board 51. The discharge switch 52 is provided on the housing 1, the discharge switch 52 is electrically connected to the control circuit board 51, and the power supply assembly is electrically connected to the control circuit board 51 via a wire. The heating insulation mechanism 4, the discharge switch 52, the operate panel 53 and the ballast 54 are electrically connected to the control circuit board 51 via wires. The ultraviolet sterilizer 8 is electrically connected to the control circuit board 51 via the ballast 54. Specifically, the ballast 54 is electrically connected to the ultraviolet sterilizer 8 via a wire, and then electrically connected to the control circuit board 51 via another wire, so as to ensure that the ultraviolet sterilizer 8 operates normally and stably and to avoid the ultraviolet sterilizer 8 from burning out when it is activated. Specifically, the discharge switch 52 is an inductive switch, the discharge switch 52 is located adjacent to the side of the discharge port, and the discharge switch 52 is provided side by side with the discharge port 61 of the liquid solenoid valve 6. The discharge switch 52 may adopt an inductive switch such as an infrared ray inductive switch. The operate panel 53 may adopt the structure of a touch screen, through which the operate panel 53 is capable of controlling the switching on and off of the automatic coupling agent feeder, setting the amount of coupling agent to be output each time and cleaning the automatic coupling agent feeder.

In one embodiment, the control device further comprises a foot switch for controlling the discharging of the automatic coupling agent feeder, the foot switch is electrically connected to the control circuit board via a wire. When in use, the automatic coupling agent feeder can be controlled to be discharged automatically by the inductive switch control, and the automatic coupling agent feeder can also be controlled to be discharged manually by controlling the foot switch.

Optionally, as shown in FIGS. 3-5, the power supply assembly includes: a charge socket 55, the charge socket 55 being embedded in the housing 1 and electrically connected to the control circuit board 51.

Further, as shown in FIGS. 3-5, the power supply assembly further comprises: a power supply board 57, the power supply board is provided within the housing, and the charge socket 55 is electrically connected to the control circuit board 51 via the power supply board 57. Specifically, the power board is electrically connected to the charge socket 55 and the control circuit board 51 respectively through a wire. The power supply assembly further comprises: a power switch 56, the power switch 56 is provided on the housing 1, and the power switch 56 is electrically connected to the power board 57 for controlling the on/off of the power supply of the automatic coupling agent feeder. Specifically, the power switch 56 is electrically connected to the charge socket 55 and the power board via wires respectively, or the power switch 56 is electrically connected to the power board 57 and the control circuit board 51 via wires respectively.

Optionally, as shown in FIGS. 3-5, the housing 1 is provided with a spacer 11 for separating the inner cavity of the housing 1 into a tank cavity 101 and an electrical cavity 102. The coupling agent storage container 2 is detachably mounted in the tank cavity 101, the tank cavity 101 is provided with a support plate 12 that is perpendicular to the spacer 11, and a tank interface 121 is provided on the support plate 12, which is adapted to the opening of the coupling agent storage container 2. The charge socket 55 and the power switch 56 are both provided on the housing 1 on a side adjacent to the tank cavity 101. The ultraviolet sterilizer 8, the heating insulation mechanism 4, the feed pump 3, the power supply board 57, the control circuit board 51, and the ballast 54 are all fixed inside the electrical cavity 102, and the operate panel 53 is provided on the housing 1 on a side adjacent to the electrical cavity 102. The ultraviolet sterilizer 8, the feed pump 3, the heating insulation mechanism 4, the power board 57 and the controller are all provided within the electrical cavity 102 to avoid exposure of the electrical components to the external environment and to reduce the risk of damage. Preferably, the coupling agent storage container 2 is a bottle product. The opening of the coupling agent storage container 2 is detachably connected to the tank interface 121 by a thread.

Further, as shown in FIGS. 3-5, the spacer 11 is fixed in a vertical direction inside the housing 1, the support plate 12 is fixed in a position adjacent to the bottom inside the tank cavity 101. A number of insertion grooves 111 are spaced apart on the inner side wall of the bottom of the tank cavity 101, and a number of insertion blocks 124 capable of being inserted one by one with the insertion grooves 111 are spaced apart on the outer side wall of the support plate 12. Optionally, the support plate 12 can be also capable of being fixed by screws inside the housing 1.

In order to enable stable installation of the parts in the electrical cavity 102, a mounting groove is provided on the spacer 11 at a side adjacent to the electrical cavity 102. The feed pump 3 is externally annularly provided with at least one fix ring 31 for stably mounting the feed pump 3 in the mounting groove, and both ends of the fix ring 31 can be screwed and fixed to the spacer 11, the ballast 54 is fixed to the spacer 11 side by side with the ultraviolet sterilizer 8, and the ballast 54 is fixed to the spacer 11 by screws. The ultraviolet sterilizer 8 is in the form of a cylinder. A clamping member 81 with a C-shape is fixed to the spacer 11, the clamping member 81 is fixed to the spacer 11 by screws, and the ultraviolet sterilizer 8 is clamped and fixed to the clamping member 81. Both the control circuit board 51 and the operate panel 53 may be fixed to the housing 1 by screws. The operate panel 53 is located in an upper part of one side of the housing 1 and above the liquid solenoid valve 6.

Optionally, as shown in FIGS. 3-5, the tank interface 121 is provided with a puncture portion 122 with a conical shape, and a number of through holes 123 are provided at intervals on the puncture portion 122, which are in communication with the tank interface 121. When in use, the user is able to unscrew the cap of the coupling agent storage container 2, and is able to rotate and mount it in the tank interface 121 without tearing off the film on the opening of the coupling agent storage container 2. When the coupling agent storage container 2 is mounted on the tank interface 121, the puncture portion 122 can open the film for use, avoiding contamination of the tank cavity 101 by dumping the coupling agent storage container 2 during mounting after the film is torn off.

Figure 2:
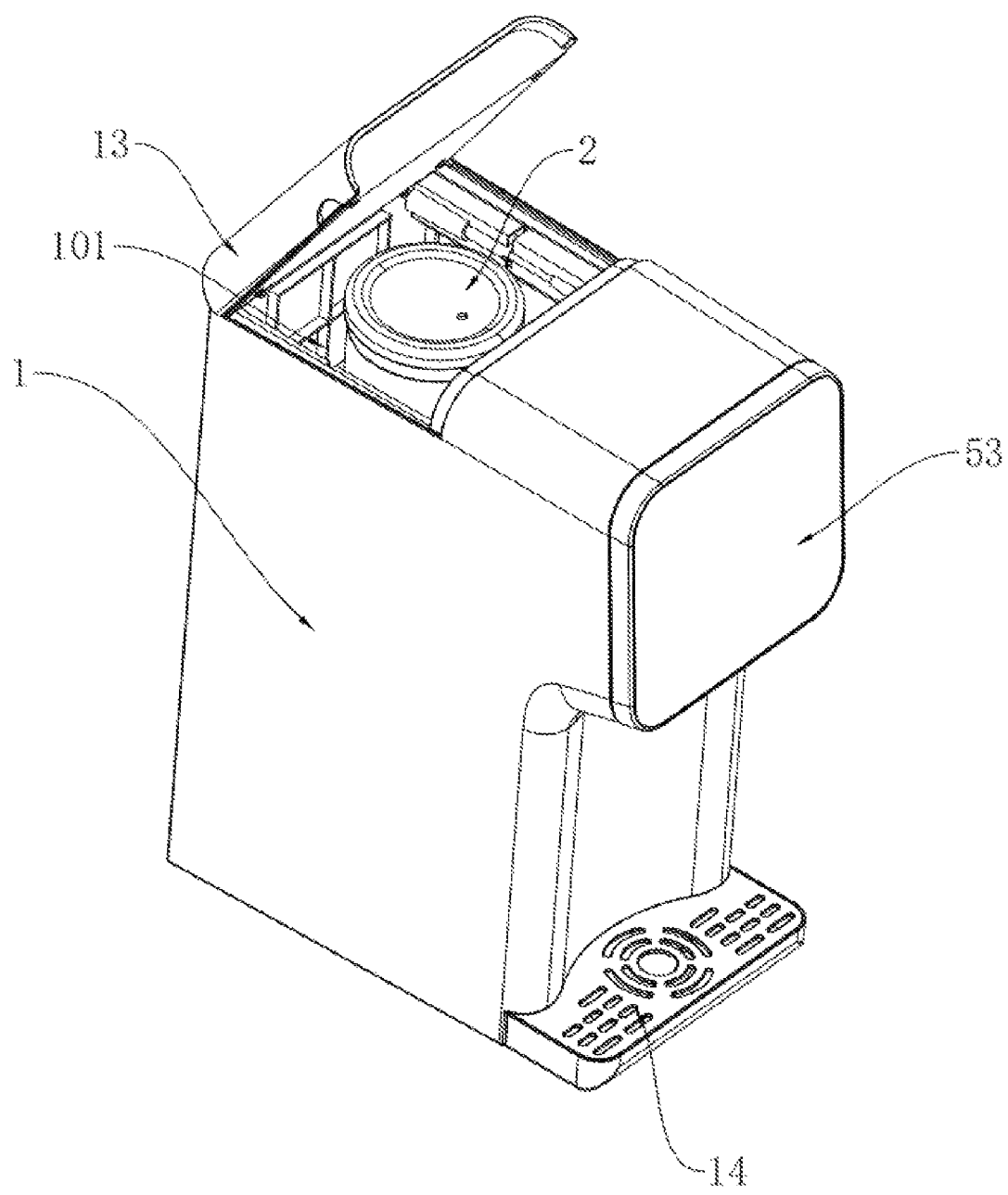
FIG. 2 is a schematic structural diagram of a top cover of Embodiment 1 in an open state.

Optionally, as shown in FIGS. 1 and 2, the housing 1 has an opening located at the top of the tank cavity 101, and a top cover 13 is hingedly connected to the housing 1 for opening or closing the opening of the tank cavity 101 to allow the user to replace the coupling agent storage container 2. Further, to facilitate the user to open the top cover 13, the top cover 13 is provided with grooves 131 on opposite sides of the top cover 13 for pivoting the user's hand, the grooves 131 are in the form of arcs but not limited to arc shapes.

Optionally, as shown in FIGS. 1-5, a receiving tray 14 is provided on the housing 1 and located directly below the discharge port 61, such that the user coupling agent falls on the ultrasonic probe through the discharge port 61. When in use, the coupling agent is heated and insulated by the heating insulation mechanism 4, such that the temperature of the coupling agent is close to the temperature of the human body when the coupling agent is output from the discharge port 61, such that the coupling agent will not be too cold when it comes into contact with the human body, and the comfort can be improved. In addition, the coupling agent is sterilized by the ultraviolet sterilizer 8, which can reduce the bacteria in the coupling agent and reduce the risk of infection. When the medical staff holds the ultrasonic probe close to the discharge switch 52, the discharge switch 52 sends a signal to the control circuit board 51, and the control circuit board 51 controls the startup of the feed pump 3, the discharge port 61 discharges the material, and the coupling agent falls on the ultrasonic probe. This method avoids contact between the medical staff and the equipment, and reduces the risk of exposure to bacteria, while allowing for one-handed operation and simpler use.

Embodiment 2

Figure 6:
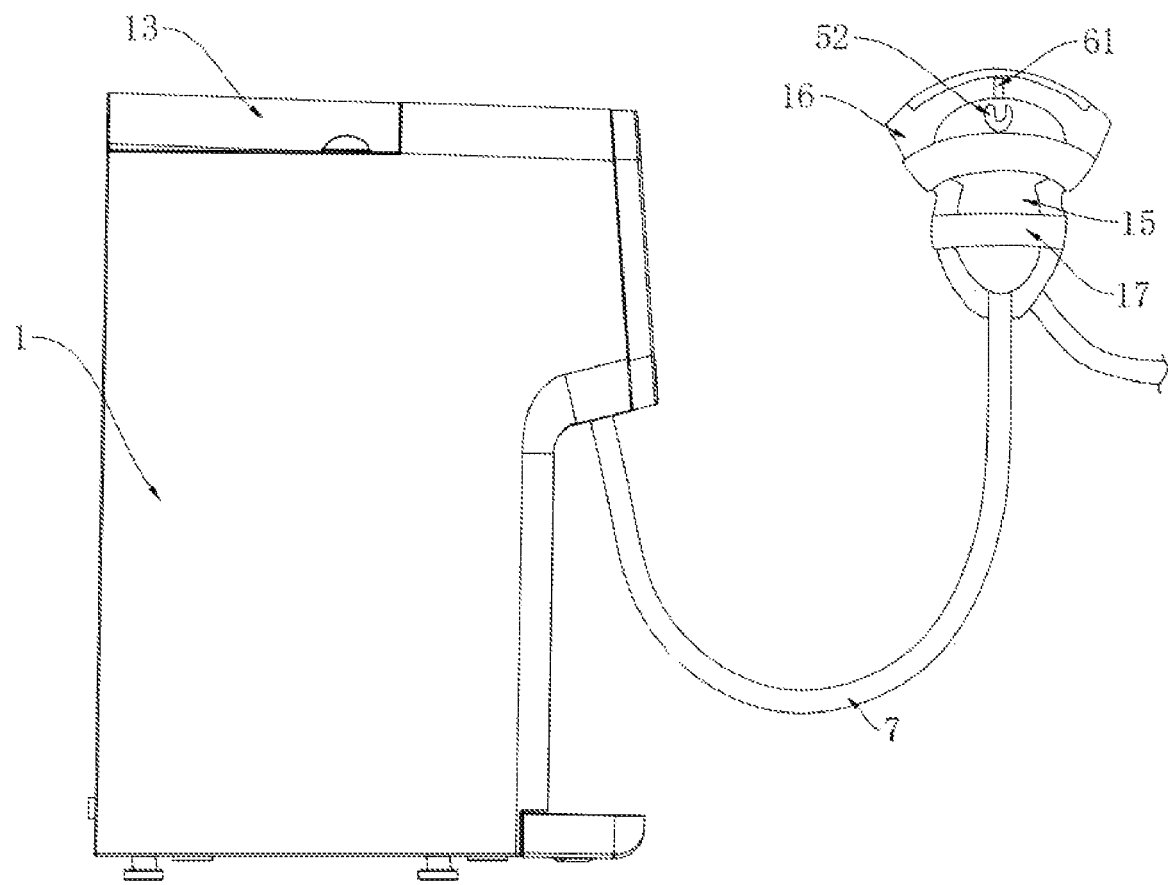
FIG. 6 is a schematic diagram of a structure of Embodiment 2.

The main difference between this embodiment and embodiment 2 is that, as shown in FIG. 6, the discharge port 61 and the discharge switch 52 of the control device 5 are not provided on the housing 1. The discharge mechanism comprises a first grip 15 and an ultrasonic probe 16. The first grip 15 is provided outside the housing 1, and the discharge port 61 is provided on the first grip 15. The discharge port 61 is connected to the feed pump 3 via the convey pipeline 7; the first grip 15 is provided with a connecting portion 17 for adapting to the ultrasonic probe 16. The connecting portion 17 may be adopted as Velcro.

In some embodiments, the discharge mechanism further comprises a liquid solenoid valve 6, the liquid solenoid valve 6 being provided within the first grip 15.

The discharge port 61 is provided on the liquid solenoid valve 6, or, the discharge port 61 is provided on the liquid solenoid valve 6.

In some embodiments, the connecting portion 17 may also be a slot provided in the first grip 15, the slot adapting to the outer contour of the ultrasonic probe 16, and the ultrasonic probe 16 can be capable of snapping onto the slot of the first grip 15.

The first grip 15 may be connected to the ultrasonic probe through the connecting portion 17, which facilitates the medical staff to hold the ultrasonic probe and the first grip 15 with one hand at the same time. When it is necessary to extrude the coupling agent, it can be done by operating the discharge switch 52 on the first grip 15, which is easy to use. The discharge switch 52 may be a contact switch or an inductive switch.

Embodiment 3

Figure 7:
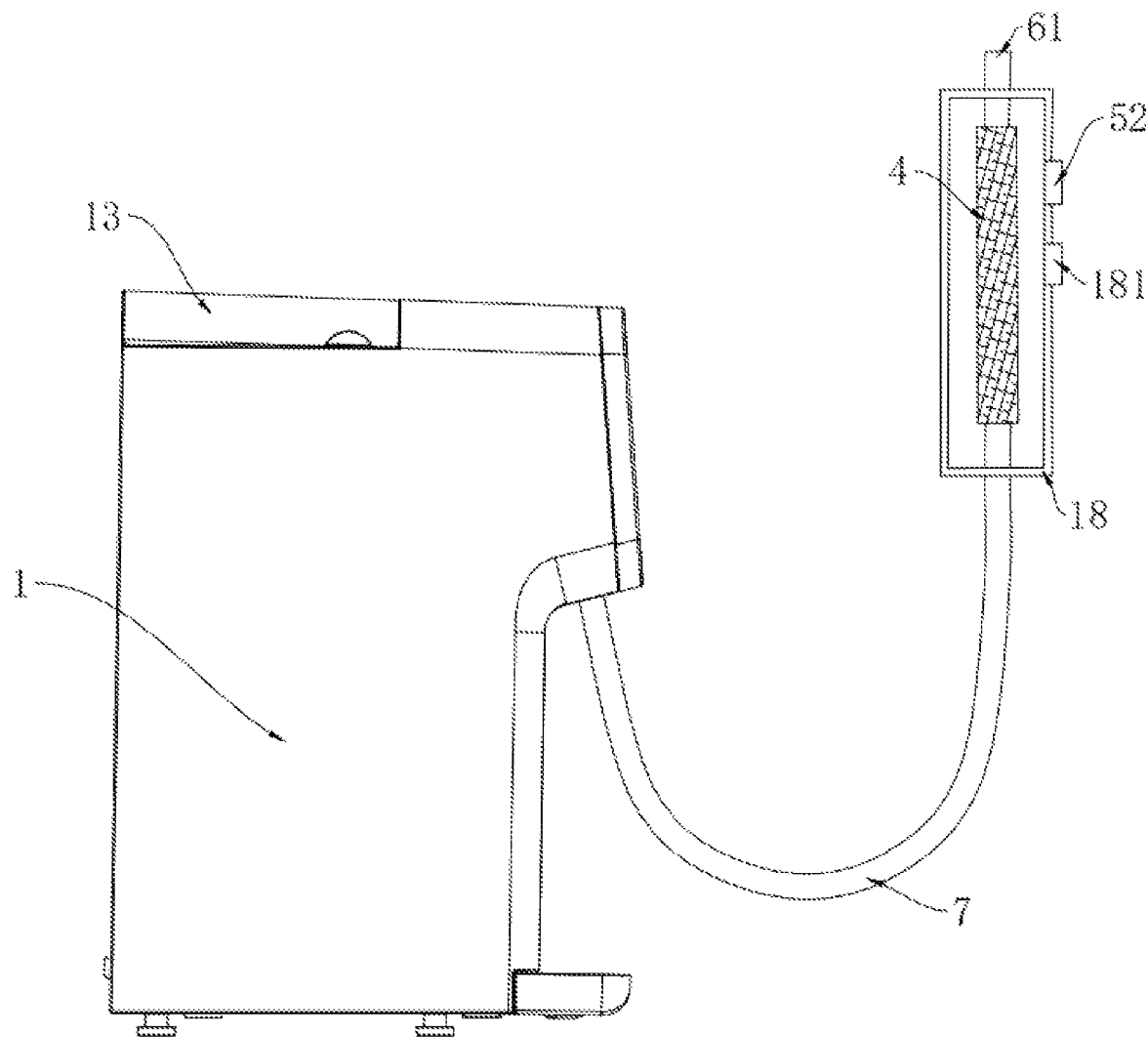
FIG. 7 is a schematic diagram of a structure of Embodiment 3.

The main difference between this embodiment and embodiment 1 is that, as shown in FIG. 7, all of the heating insulation mechanism 4, the discharge port 61 and the discharge switch 52 are not provided on the housing 1. An automatic coupling agent feeder comprises: the housing 1, the coupling agent storage container 2, the feed pump 3, the heating insulation mechanism 4, the control device 5, and the discharge mechanism. The coupling agent storage container 2, the feed pump 3 and the discharge mechanism are provided in the housing 1. The feed pump 3 is connected to the coupling agent storage container 2 and the discharge mechanism respectively through the convey pipeline 7. The discharge mechanism comprises a second grip 18; the second grip 18 is provided outside the housing 1, and the second grip 18 is provided with the discharge port 61; the discharge port 61 is connected to the outlet end of the feed pump 3 through the convey pipeline 7. The heating insulation mechanism 4 is sleeved on the convey pipeline 7 and is situated in the second grip 18. The control device 5 is electrically connected to the feed pump 3 and the heating insulation mechanism 4, respectively. The control device 5 is electrically connected to the feed pump 3 and the heating insulation mechanism 4 respectively. The discharge switch 52 of the control device 5 is provided on the second grip 18, which is also provided with a heating switch 181, and both the heating switch 181 and the heating insulation mechanism 4 are electrically connected to the control circuit board 51 of the control device 5. The inner wall of the second grip 18 is provided with a heat-insulating material to provide heat insulation. In some embodiments, the discharge mechanism further includes a liquid solenoid valve 6, the liquid solenoid valve 6 is provided in the second grip 18. The discharge port 61 is provided on the liquid solenoid valve 6, or, the discharge port 61 is in communication with the liquid solenoid valve 6, and the convey pipeline 7 extends to the second grip 18 and is in communication with the liquid solenoid valve 6.

Specifically, the medical staff may hold the ultrasonic probe in one hand and the second grip 18 in the other hand, and heat and insulate the coupling agent in the heating insulator by means of the heating switch 181 on the second grip 18, and then control the coupling agent to be extruded out of the discharge port 61 by means of the discharge switch 52, such that it is easy to operate.

The above are only to illustrate the technical solutions of the present disclosure rather than limitations. Any other modifications or equivalent replacements made by those skilled in the art in the field to the technical solution of the present disclosure, as long as they do not depart from the spirit and scope of the technical solution of the present disclosure, should be encompassed within the scope of the claims of the present disclosure.

What is claimed is:

1. An automatic coupling agent feeder, comprising: a housing, a coupling agent storage container, a feed pump, a heating insulation mechanism, a control device, and a discharge mechanism;
   wherein the coupling agent storage container and the feed pump are provided in the housing, the discharge mechanism is provided with a discharge port located outside the housing; wherein the discharge mechanism further comprises a liquid solenoid valve connected to an outlet end of the convey pipeline, and electrically connected to the control device;
   the control device is provided on the housing and is electrically connected to the feed pump and the heating insulation mechanism;
   the feed pump is connected to the coupling agent storage container and the discharge mechanism, respectively, by means of a convey pipeline, and the heating insulation mechanism is provided outside the convey pipeline between the feed pump and the discharge mechanism;
   wherein the control device further comprises a control circuit board, a discharge switch, an operate panel, a ballast and a power supply assembly; the control circuit board, the ballast and the power supply assembly are provided in the housing, the operate panel is provided on the housing and is electrically connected to the control circuit board; the power supply assembly is electrically connected to the control circuit board; the ultraviolet sterilizer is electrically connected to the control circuit board by the ballast.

2. The automatic coupling agent feeder according to claim 1, wherein the power supply assembly comprises a charge socket embedded in the housing and electrically connected to the control circuit board.

3. The automatic coupling agent feeder according to claim 1, wherein the power supply assembly further comprises a power board provided in the housing, and the charge socket is electrically connected to the control circuit board via the power board.

4. The automatic coupling agent feeder according to claim 1, wherein the power supply assembly further comprises a power switch provided on the housing, and is electrically connected to the power board.

5. The automatic coupling agent feeder according to claim 1, wherein the housing is provided with a spacer for separating an inner cavity of the housing into a tank cavity and an electrical cavity, the coupling agent storage container is detachably mounted in the tank cavity; the tank cavity is provided with a support plate perpendicular to the spacer, the support plate is provided with a tank interface adapted with an opening of the coupling agent storage container; the charge socket and the power switch are both provided on a side of the housing adjacent to the tank cavity, the ultraviolet sterilizer, the heating insulation mechanism, the feed pump, the power board, the control circuit board and the ballast are all fixed in the electrical cavity, and the operate panel is provided on a side of the housing adjacent to the electrical cavity.

6. The automatic coupling agent feeder according to claim 1, wherein the tank interface is provided with a puncture portion with a conical shape, and the puncture portion is provided with a number of through holes spaced apart in communication with the tank interface.

7. The automatic coupling agent feeder according to claim 1, wherein the housing has an opening located at a top of the tank cavity, and the housing is hingedly connected to a top cover for opening or closing the opening of the tank cavity.

8. The automatic coupling agent feeder according to claim 1, wherein the discharge mechanism comprises a first grip and an ultrasonic wave probe; the first grip is provided outside the housing, and the discharge port is provided on the first grip; the discharge port is connected to the feed pump through the convey pipeline; and the first grip is provided with a connecting portion for adapting to the ultrasonic wave probe.

9. An automatic coupling agent feeder, comprising: a housing, a coupling agent storage container, a feed pump, a heating insulation mechanism, a control device and a discharge mechanism;
   wherein the coupling agent storage container, the feed pump and the discharge mechanism are all provided in the housing; the feed pump is connected to the coupling agent storage container and the discharge mechanism through a convey pipeline respectively;
   the discharge mechanism comprises a second grip provided outside the housing and provided with a discharge port; the discharge port is connected to an outlet end of the feed pump through the convey pipeline; the heating insulation mechanism is provided on the convey pipeline and is located inside the second grip;
   the control device is electrically connected to the feed pump and the heating insulation mechanism, respectively.

* * * * *